United States Patent
Miles et al.

(10) Patent No.: US 7,049,461 B1
(45) Date of Patent: May 23, 2006

(54) TREATMENT OF LEUKEMIA

(75) Inventors: D. Howard Miles, Winter Springs, FL (US); Solodnikov Sergey Yurjevich, Perm (RU); Krasnykh Olga Petrovna, Perm (RU); Malanin Vladimir Vladmirovitch, Perm (RU); Tatiana A. Korotkova, Stanford, CA (US)

(73) Assignee: University of Central Florida, Orlando, FL (US)

( * ) Notice: Subject to any disclaimer, the term of this patent is extended or adjusted under 35 U.S.C. 154(b) by 640 days.

(21) Appl. No.: 10/164,857

(22) Filed: Jun. 7, 2002

Related U.S. Application Data

(60) Provisional application No. 60/296,823, filed on Jun. 8, 2001.

(51) Int. Cl.
*C07C 69/66* (2006.01)

(52) U.S. Cl. .................. 560/174; 560/174; 560/129
(58) Field of Classification Search ............... 560/129, 560/5, 174
See application file for complete search history.

(56) References Cited

U.S. PATENT DOCUMENTS

| | | | |
|---|---|---|---|
| 5,308,852 A | 5/1994 | Girard | 514/336 |
| 5,334,612 A | 8/1994 | Kalden | 514/440 |
| 6,048,896 A | 4/2000 | Giordani | 514/545 |
| 6,066,670 A | 5/2000 | Brown | 514/557 |
| 6,121,450 A | 9/2000 | Jones | 546/81 |
| 6,180,651 B1 | 1/2001 | Nicolai | 514/336 |
| 6,232,312 B1 | 5/2001 | Pamukcu | 514/237.5 |

*Primary Examiner*—Joanne Richter
*Assistant Examiner*—Karl Puttlitz
(74) *Attorney, Agent, or Firm*—Brian S. Steinberger; Roland Dexter; Law Offices of Brian S. Steinberger, P.A.

(57) ABSTRACT

A preferred embodiment of the invention encompasses a compounds having the property of anti-carcinogenic activity against human leukemia comprising the use of 4-(4-Ethoxy-phenyl)-2-(N'-fluoren-9-ylidene-hydrazino)-2-hydroxy-4-oxo-butyric acid methyl ester (OF-13), and/or 4-Chloro-4-(4-ethoxy-phenyl)-2-(fluoren-9-ylidene-hydrazono)-but-3-enoic acid methyl ester (3F-19) in humans as therapeutic means for the eradication of leukemia from the human's body.

2 Claims, 1 Drawing Sheet

TREATMENT OF LEUKEMIA

This invention relates to the novel compounds which are derivatives of oxo-butenoic acid and their use alone or in combination for treatment of human leukemia and claims the benefit of priority to U.S. Provisional Application Ser. No. 60/296,823 filed Jun. 8, 2001.

FIELD OF THE INVENTION

BACKGROUND OF THE INVENTION

Cancer is a global killer of humans with breast cancer and colon cancer among the leaders with many other types killing modest amounts of humans yearly.

Two blood cancers are of interest because there is no known cure, i.e. myeloma and leukemia.

Leukemia is a type of cancer which is one of more than 100 diseases that have two important things in common. One is that certain cells in the body become abnormal. Second is that after this development, the human body keeps producing large numbers of these abnormal cells.

Leukemia is cancer of the blood cells and develops (as noted) when the human body produces large numbers of abnormal blood cells. In most types of leukemia, the abnormal cells are white blood cells. The leukemia cells usually look different from normal blood cells, and they do not function properly.

Since this cancer is complex in nature and not susceptible to any specific therapy, there are a number of treatments employed including chemotherapy when drugs are employed, biological with the use of interferon, radiation and bone marrow transplants.

Each year, nearly 27,000 adults and more than 2,000 children in the United States learn that they have leukemia for which there is no cure only palliative treatment.

The U.S. patent literature has many disclosures of heterocyclic oxo-butenoic (crotonic) compounds:

Pamukci (U.S. Pat. No. 6,232,312) describes crotonic acid derivatives (column 22, lines 43–58) for the treatment of colonic polyps;

Jones et al (U.S. Pat. No. 6,121,450) discloses crotonic acid derivatives (column 8, tine 34; column 78, line 24 and at example 34 as steroid modifiers in treating breast cancer (column 1, lines 55–58);

Kalden, et al (U.S. Pat. No. 5,334,612) discloses compounds said to be useful for treating AIDS including derivatives of carboxylic acid (column 9, line 31) and pyrrolidine (column 7, line 24);

Brown (U.S. Pat. No. 6,066,670) describes an anti-viral admixture containing crotonic acid for treating tumors (see Abstract);

Horwell, et al (U.S. Pat. No. 5,580,896) discloses many 4-oxo-2-butenoic acid derivatives (column 13, lines 21–59; also in columns 15+, examples 25,26,32,34,40, 43–46,77–79,97,99,103,106,), which are useful for inhibiting colorectal cancer, i.e., colon cancer (Abstract);

Giordani, et al (U.S. Pat. No. 5,580,890) discloses 4-oxo-2-butenoic acid derivatives said to be useful for treatment of AIDS (column 1, line 8 and column 2, line 61; and, Yonemeto, et al (U.S. Pat. No. 6,083,985) recites a number of anti-tumor or anti-AIDS agents that include butenoic acid derivatives.

It appears from a review of the foregoing that the oxo-butenoic derivatives of interest are not disclosed and thus there is no report of their activity against human leukemia.

Consequently, there is a need for an anti-cancer drug for humans that mitigates the above mentioned disadvantages of current drug therapy and effectiveness against human leukemia.

SUMMARY OF THE INVENTION

The objective of the present invention is to provide a novel compound effective for treatment of human leukemia.

A preferred embodiment of the invention encompasses a novel compound: 4-(4-Ethoxy-phenyl)-2-(N'-fluoren-9-ylidene-hydrazino)-2-hydroxy-4-oxo-butyric acid methyl ester and compounds having the property of anti-cancer activity against human leukemia comprising the use of 4-(4-Ethoxy-phenyl)-2-(N'-fluoren-9-ylidene-hydrazino)-2-hydroxy-4-oxo-butyric acid methyl ester (OF-13), and/or 4-Chloro-4-(4-ethoxy-phenyl)-2-(fluoren-9-ylidene-hydrazono)-but-3-enoic acid methyl ester (3F-19) in humans as therapeutic means for the eradication of leukemia from the human's body.

Further objects and advantages of this invention will be apparent from the following detailed description of presently preferred embodiments which are illustrated structurally in the accompanying drawings.

DESCRIPTION OF THE PREFERRED EMBODIMENTS

Before explaining the disclosed embodiments of the present invention in detail, it is to be understood that the invention is not limited in its application to the details of the particular arrangement shown since the invention is capable of other embodiments. Also, the terminology used herein is for the purpose of description and not of limitation.

Figure 1:
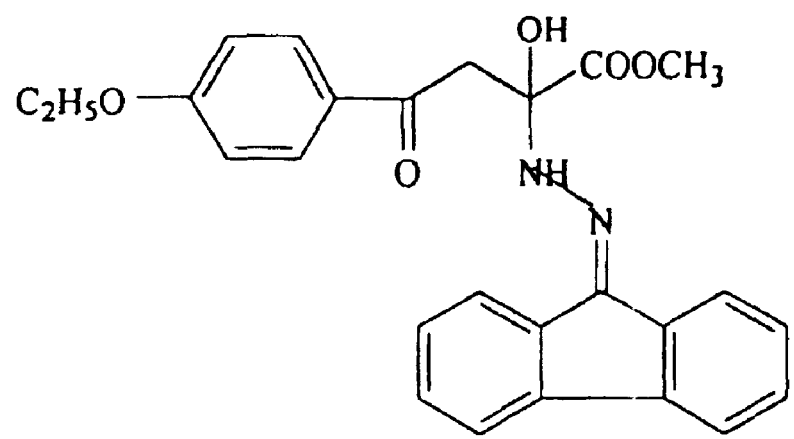
FIG. 1 illustrates structurally a chemical compound designated as OF-13.
Figure 2:
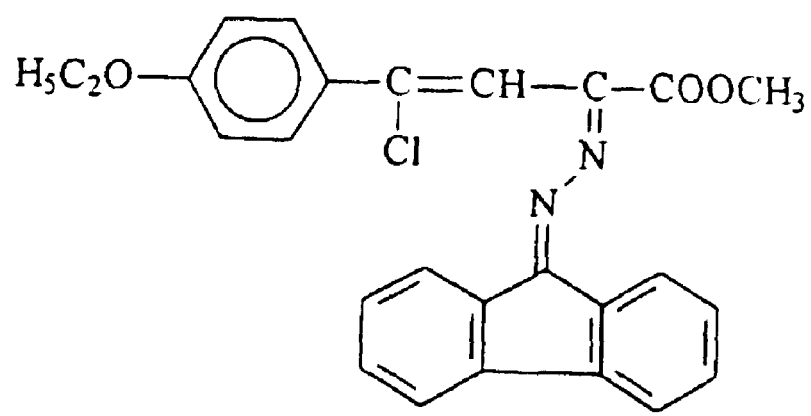
FIG. 2 illustrates structurally a chemical compound designated as 3F-19.

This application is directed to the use of the compounds OF-13 and 3F-19, alone or in combination, which have been structurally shown in FIGS. 1 and 2 respectively, to treat human leukemia.

To facilitate a full understanding of the invention:
the compound designated as OF-13 is 4-(4-Ethoxy-phenyl)-2-(N'-fluoren-9-ylidene-hydrazino)-2-hydroxy-4-oxo-butyric acid methyl ester (claimed herein) and, the compound designated as 3F-19 is methyl 4-Chloro-4-(4-ethoxy-phenyl)-2-(fluoren-9-ylidene-hydrazino)-but-3-enoic acid methyl ester.

These compounds have very high activity against leukemia and a very low toxicity as Lethal Dose 50 ($LD_{50}$) in animals. The percent activity and animal toxicity for each compound is as follows: OF-13 (97% against human leukemia and $LD_{50}$>1500 mg/kg), and 3F-19 (100% against human leukemia and $LD_{50}$>200 mg/kg).

PREPARATION OF (OF-13)

EXAMPLE 1

The preparation of 4-(4-Ethoxyphenyl)-2-(N'-fluoren-9-ylidene-hydrazino)-2-hydroxy-4-oxobutyric acid methyl ester (OF-13). A solution of 5.0 g (0.02 moles) of methyl 4-p-ethoxyphenyl-2-hydroxy-4-oxo-2-butenoate (1) and 3.88 g (0.02 moles) of fluorene-9-ylidene-hydrazine (2) in 80 mL of absolute benzene and absolute toluene (1:1) was refluxed for 1 hr 30 min with a Dean-Stark trap (the end of the reaction was determined by TLC), cooled and the precipitate was filtered and recrystallized from benzene-diethyl ether-hexane mixture (1:3:2) to give 2.65 g (53% yield) of colorless crystals with mp 114–116° C.

Solubility: highly soluble in DMSO, DMFA, dichloroethane, acetonitrile, insoluble in hexane. The compound is not stable in solutions and decomposes quickly when the solution is heated or stored for a long time with the formation of OF-12.

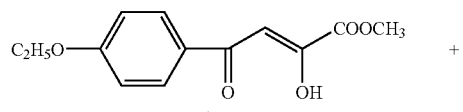

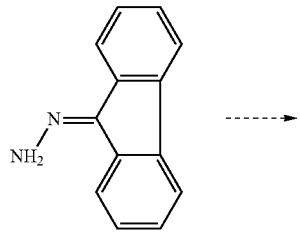

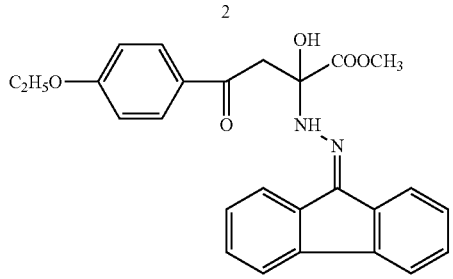

OF-13

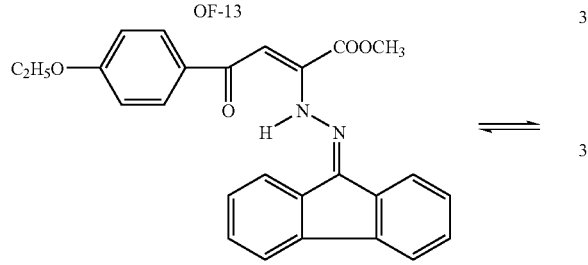

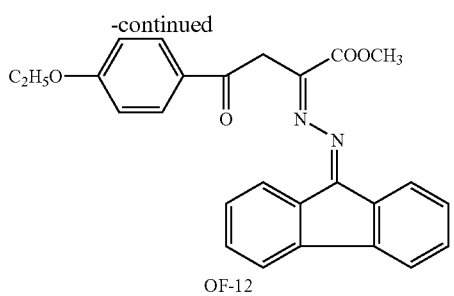

OF-12

It is seen from the foregoing that (OF-13) is an intermediate product during the synthesis of (OF-12).

PREPARATION OF (3F-19) (also included as a "structure-use" in UCF-311B)

EXAMPLE 2

The preparation of 4-Chloro-4-(4-ethoxy-phenyl)-2-(fluoren-9-ylidene-hydrazono)-but-3-enoic acid methyl ester (3F-19) To the solution of 10 g (0.0026 moles) of 4-(4-Ethoxy-phenyl)-2-(N'-fluoren-9-ylidene-hydrazino)-4-oxo-but-2-enoic acid methyl ester (1) (synthesis was previously published by Konyukhova, N. A.; Krasnykh, O. P.; Aliev, Z. G.; Maslivets, A. N. *Chemistry of Heterocyclic Compounds* (New York, N.Y., United States)(Translation of *Khimiya Geterotsiklicheskikh Soedinenii*) (2001), 37(6), 779–780) in 5 mL of anhydrous benzene 0.3935 g (0.0031 moles) oxalyl chloride was added. The reaction mixture was refluxed for 1 hour 40 min, cooled, precipitate was filtered and recrystallized from absolute benzene to give 0.62 g (54%) of yellow crystals, m.p. 163–163 (decomp).

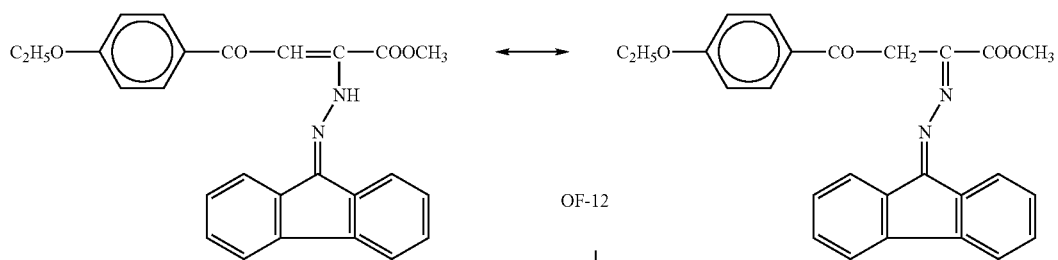

OF-12

(COCl)$_2$

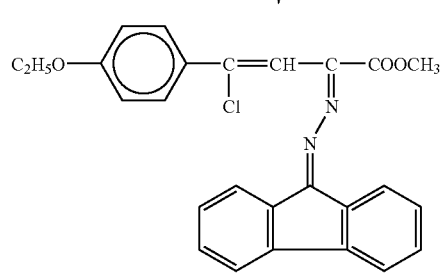

3F-19

CYTOTOXICITY ASSAY

The activity against leukemia cancer cells of the compounds (as earlier reported) was realized by the following procedure which determines the inhibitory effect of test samples on the growth of human leukemia cancer cells (ATCC JURK). The Jurkat cells are grown in RPMI 1640 media+10% Fetal bovine serum+1% Antibiotic/Antimycotic+1% of HEPES Buffer (1M)+1% Sodium Purivate (100 mM)+2.5% D-(+) Glucose Solution for approximately 48 hours at 37° C./5% $CO_2$ in the presence of the test in the presence of the test compound.

Growth/Non-Growth of the cells (e.g., cell density) is determined using Promega's MTS/PMS assay system. MTS (3-(4,5-dimethylthiazol-2-yl)-5-(3-carboxymethoxyphenyl)-2-(4-sulfophenyl)-2H-tetrazolium, inner salt) is an aqueous compound that is reduced to soluble formazan by the presence of NADH formed by dehydrogenases present within the Jurkat cells. The absorbance of the formazan can be measured at 490 nm and is directly proportional to the number of living cells present in the culture. PMS (Phenazine Methosulfate) is added an electron coupling reagent and greatly increases the rate of reduction.

To facilitate a full understanding of the procedure the following definitions are offered:
- Test wells—wells containing test sample and Diluted Jurkat cells
- Test values—absorbance of test wells
- Blank wells—wells containing test sample and Jurkat media (JURK-01S); used to obtain background absorbance due to test sample
- Blank values—absorbance of blank wells
- Negative Control—maximal cell growth; results of test samples will be expressed as a percent of the Negative Control
- Positive Control—known inhibitor of Jurkat cells; used to validate assay system
- Matrix—solvent that the samples are prepared/diluted in
- Assay samples of similar origin and matrix (e.g., methanol extraction, methylene chloride extraction, water soluble samples, etc.) together on the same plate in order to reduce the number of steps performed per plate.
- Blank values will be determined for each sample to account for any color contribution due to the sample itself. These blank wells must contain the same amount of sample plus Jurkat media (no cells). After completion of MTS/PMS reaction blank values will be subtracted from the test value to obtain a net absorbance that will be used to calculate cell density.

All results are based upon a comparison to the Negative Control value of the plate. The Negative Control must contain the same amount of matrix (e.g., solvent) to offset any destructive effect the matrix may have on the growth of the Jurkat cells (allows for baseline values to be set).

For most samples, a Jurkat cell growth (initial density of 120,000 to 180,000 cells/ml) of approximately 48 hours followed by and incubation of 2 hours with the MTS/PMS Reagent is optimal.

In order to establish the accuracy of this assay a Positive Control consisting of 50 μM Methotrexate should not decrease the net absorbance to less than 90% of the Negative Control (Jurkat cells are somewhat resistant to methotrexate) is utilized.

ANIMAL TOXICITY BIOASSAY

Acute toxicity was studied on white mice of both sexes with weight ranging between 18–26 grams under intraperitoneal injection of 2% solution of tested compound in starch (the compound was dissolved in starch slime and injected) on the basis of 0.1 ml of solution per 10 g of the animal weight. Each dose was tested on the group of 6 animals that were observed during 14 days period. (This method was approved by the Pharmacology committee of Russian Ministry of Health and has been widely used since 1968.) Averaged lethal dose ($LD_{50}$) of the compound was computed using results of experiments on 5–7 groups of animals using method of Litchfield and Wilkinson. (Belenkii M. L. "Elements of quantative determination of the pharmacological effect," Leningrad, 1963, 71 pages).

USE OF THE INVENTION FOR TREATMENT OF LEUKEMIA CANCER

The compounds of the invention which are useful for the treatment of leukemia are 4-(4-Ethoxy-phenyl)-2-(N'-fluoren-9-ylidene-hydrazino)-2-hydroxy-4-oxo-butyric acid methyl ester (OF-13), and 4-Chloro-4-(4-ethoxy-phenyl)-2-(fluoren-9-ylidene-hydrazono)-but-3-enoic acid methyl ester (3F-19) for in vivo use in humans as therapeutic means for the eradication of leukemia can be used in a pharmaceutical composition comprising a non-toxic effective amount of the referenced compounds, alone or together, or a tautomeric form thereof or a pharmaceutically acceptable salt thereof or pharmaceutically acceptable solvate thereof, and a pharmaceutically acceptable carrier thereof.

For administration to man in the curative or prophylactic treatment of human colon cancer in vivo dosages of compounds of the invention will generally be in the range of from 5 to 500 mg daily for an average adult patient (70 kg). Thus for a typical adult patient, individual tablets or capsules contain from 2–500 mg of active compound, in a suitable pharmaceutically acceptable vehicle or carrier, for administration in single or multiple doses, once or several times per day. Exemplary dosages for intraveneous, buccal or sublingual administration will typically be within the range of from 5–1000 mg per single dose as required. In practice the physician will determine the actual dosing administration by periodically monitoring the abnormal (generally white) cell content of the blood which will be most suitable for an individual patient and it will vary with the age, weight and response of the particular patient. The above dosages are exemplary of the average case but there can be individual instances in which higher or lower dosage ranges may be merited, and such are within the scope of this invention.

The maximum human one time administration dose for the compound(s) of the invention appears to be 100 and 750 mg for 3F-19 and OF-13, respectiively.

For human use, the compounds of the invention can be administered alone or jointly, but will generally be administered in admixture with a pharmaceutical carrier selected with regard to the intended route of administration and standard pharmaceutical practice. For example, they may be administered orally, buccally or sublingually, in the form of tablets containing excipients such as starch or lactose, or in capsules or ovules either alone or in admixture with excipients, or in the form of elixirs or suspensions containing flavouring or colouring agents. The compounds may also be injected parenterally, for example intraveneously, intramuscularly, subcutaneously or intracoronarily. For parenteral administration, they are best used in the form of a sterile aqueous solution, which may contain other substances, for example enough salts or glucose to make the solution isotonic with blood.

The invention thus provides a method for the treatment of leukemia in a human mammal which comprises administering an effective, non-toxic, amount of a heterocyclic compound according to the invention or a tautomeric form thereof and/or a pharmaceutically acceptable salt thereof and/or a pharmaceutically acceptable solvate thereof, to a leukemia invaded human mammal in need thereof.

ADVANTAGES OF THE INVENTION

Chemotherapy for leukemia is varied, because there are many different forms of this disease. In general, though, leukemia treatment relies on combination chemotherapy with a number of different anticancer drugs. Such drugs destroy cancer cells by preventing them from growing and dividing rapidly. Unfortunately, a number of the body's normal, noncancerous cells also divide rapidly and therefore are harmed by chemotherapy.

Typical drug combination used in chemotherapy treatment of Acute Myelogenous Leukemia (AML) is a combination of daunorubicin (toxicity in mice LD50 26 mg kg$^{-1}$) with cytarabine (toxicity: in mice LD50 826 mg kg$^{-1}$). These toxicities should be compared with the toxicity of claimed compounds that lie in the range 1000–1500 mg kg$^{-1}$ in mice. It can be seen that the claimed compound has toxicity at leas 50 times lower than daunorubicin and it is no more toxic than cytarabine.

There is a variety of the side effects to this treatment. Daunorubicin—myelosuppression (impaired bone marrow function), cardiotoxicity (heart damage), gastrointestinal effects; cytarabine—gastrointestinal effects (nausea, vomiting, diarrhea), bleeding, fever.

Another approach to the leukemia treatment is by employing interferons. Interferons are a class of proteins that are released by virus-infected cells. They help normal cells to make antiviral proteins. Interferons also help the body to reduce leukemia cell proliferation (growth and reproduction), while strengthening the body's immune response. Unfortunately, though, this drug is not without side effects. Possible IFN-related complaints include fevers, chills, muscle aches, bone pain, headaches, concentration difficulties, fatigue, nausea, vomiting, and general flu-like symptoms when starting the drug.

It appears that the disclosed compounds create a means for further development of anti-leukemia drugs with lower toxicity and less side effects.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A compound which is 4-(4-Ethoxy-phenyl)-2-(N'-fluoren-9-ylidene-hydrazino)-2-hydroxy-4-oxo-butyric acid methyl ester.

2. A method of treating a human having leukemia which comprises administering a non-toxic amount of a compound according to claim 1 to said human.

* * * * *